US008739778B2

(12) United States Patent
Tappehorn et al.

(10) Patent No.: US 8,739,778 B2

(45) Date of Patent: Jun. 3, 2014

(54) BREATHING TUBE CONNECTING DEVICE

(75) Inventors: Ludger Tappehorn, Lübeck (DE); Olaf Schermeier, Lübeck (DE); Gerd Wotha, Warnsdorf (DE); Klaus Abraham, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1362 days.

(21) Appl. No.: 12/514,664

(22) PCT Filed: Nov. 3, 2007

(86) PCT No.: PCT/DE2007/001975

§ 371 (c)(1), (2), (4) Date: May 13, 2009

(87) PCT Pub. No.: WO2008/058506

PCT Pub. Date: May 22, 2008

(65) Prior Publication Data

US 2010/0059057 A1 Mar. 11, 2010

(30) Foreign Application Priority Data

Nov. 14, 2006 (DE) ......................... 10 2006 053 857

(51) Int. Cl.
*A61M 16/08* (2006.01)

(52) U.S. Cl.
USPC ................... 128/202.27; 128/200.24; 285/45; 285/148.3; 285/330

(58) Field of Classification Search
USPC .................. 128/204.18, 204.23, 204.25, 912, 128/200.24, 202.22, 202.27; 285/9.2, 45, 285/148.3, 330, 399, 903; 604/905, 94.01, 604/173, 258
See application file for complete search history.

(56) References Cited

U.S. PATENT DOCUMENTS 3,388,705 A * 6/1968 Grosshandler ........... 128/207.14
3,707,301 A * 12/1972 Rauls ............................ 285/9.2
4,475,548 A * 10/1984 Muto ....................... 128/207.14
4,825,859 A * 5/1989 Lambert .................. 128/202.16
4,827,921 A * 5/1989 Rugheimer .............. 128/202.27
4,850,984 A * 7/1989 Harris ........................... 604/326
4,852,564 A * 8/1989 Sheridan et al. ......... 128/202.27
5,116,088 A * 5/1992 Bird ............................. 285/319
5,176,415 A * 1/1993 Choksi .......................... 285/331

(Continued)

FOREIGN PATENT DOCUMENTS

CA 2153614 A1 1/1996
DE 10014178 A1 9/2001

(Continued)

*Primary Examiner* — Jackie T Ho
*Assistant Examiner* — Eric Bryant
(74) *Attorney, Agent, or Firm* — McGlew and Tuttle, P.C.

(57) ABSTRACT

A breathing tube connecting device is provided for connecting a breathing tube to at least two respirators. The breathing tube connecting device includes a base body with a breathing gas through duct embodied in the base body, a jacket body, which can be meshed with the base body in a positive-locking manner and thus encloses at least a part of the base body in a coaxial manner, and a transponder. The transponder is provided between the base body and the jacket body. The breathing gas through duct and the jacket body are embodied at least partly as a coupling section for a selective connection of the breathing tube to one of the at least two respirators.

20 Claims, 2 Drawing Sheets

(56) References Cited

U.S. PATENT DOCUMENTS 5,285,776 A * 2/1994 Bertram .................. 128/207.14
5,315,991 A * 5/1994 Teves ...................... 128/207.14
5,333,606 A * 8/1994 Schneider et al. ....... 128/200.24
5,359,999 A * 11/1994 Kinsman ................. 128/204.21
5,579,762 A * 12/1996 Lee ........................ 128/207.14
5,582,166 A * 12/1996 Lee ........................ 128/207.14
5,702,374 A * 12/1997 Johnson ....................... 604/533
5,722,391 A 3/1998 Rosenkoetter et al.
5,722,392 A * 3/1998 Skimming et al. ....... 128/203.12
5,771,888 A * 6/1998 Keim ...................... 128/207.15
5,787,879 A * 8/1998 Gibson ................... 128/202.27
5,794,986 A * 8/1998 Gansel et al. ........... 285/148.16
6,415,789 B1 * 7/2002 Freitas et al. ........... 128/202.27
6,484,724 B1 * 11/2002 Sloan ...................... 128/207.17
6,488,026 B2 * 12/2002 Lauer ...................... 128/202.27
6,669,681 B2 * 12/2003 Jepson et al. ................ 604/533
6,877,511 B2 * 4/2005 DeVries et al. .......... 128/204.26
6,953,354 B2 * 10/2005 Edirisuriya et al. .......... 439/191
6,974,447 B2 * 12/2005 Smith et al. .................. 604/415
7,174,889 B2 * 2/2007 Boedeker et al. ........ 128/200.26
7,500,483 B2 * 3/2009 Colman et al. ........... 128/207.14
7,828,780 B2 * 11/2010 Chu et al. ..................... 604/248
7,901,361 B2 * 3/2011 Rapoport et al. ............. 600/533
RE43,142 E * 1/2012 Jepson et al. ................. 604/256
2002/0124845 A1 * 9/2002 Lauer ....................... 128/202.27
2003/0236015 A1 * 12/2003 Edirisuriya et al. .......... 439/191
2004/0017321 A1 * 1/2004 Benedict et al. .............. 343/741
2005/0279362 A1 * 12/2005 Colman et al. ........... 128/207.14
2006/0096597 A1 * 5/2006 Amann ................... 128/205.27
2008/0066756 A1 3/2008 Lang et al.
2009/0088656 A1 * 4/2009 Levitsky et al. .............. 600/532

FOREIGN PATENT DOCUMENTS

DE 10 2005 001247 7/2006
EP 1 138 340 10/2001
EP 1 520 599 4/2005
WO 2006/015772 A1 2/2006

* cited by examiner

BREATHING TUBE CONNECTING DEVICE

CROSS REFERENCE TO RELATED APPLICATIONS

This application is a United States National Phase application of International Application PCT/DE2007/001975 and claims the benefit of priority under 35 U.S.C. §119 of German Patent DE 10 2006 053 857.9 filed Nov. 14, 2006, the entire contents of which are incorporated herein by reference.

FIELD OF THE INVENTION

The present invention pertains to a breathing tube connecting device for connecting a breathing tube to at least two respirators.

BACKGROUND OF THE INVENTION

Breathing tube connecting devices are used in a known manner for connecting a breathing tube or a breathing tube system, designated as breathing tube below for the sake of simplicity, to a respirator. A respirator may comprise an anesthesia apparatus. The breathing tube connecting devices differ with respect to the diameter of a breathing gas through duct. Thus, breathing tube connecting devices for neonatal use have smaller diameters compared to breathing tube connecting devices for connecting a breathing tube to a respirator for adults. Breathing tube connecting devices have either a male or female connection. A connection complementary thereto can be found in each case on the respirator. Breathing tube connecting devices for a connection to a neonatal respirator are usually designed with a female connection, whereas breathing tube connecting devices for a connection to a respirator for adults can be designed with a male or female connection. On the other hand, the connections to the neonatal respirator are usually designed as a male connection and the connections to the adult respirator are designed as a combination of male and female connections.

For the breathing tube connecting devices there is a current standard of 11, 15 and 22 mm diameters of the breathing gas through duct. Here, breathing tube connecting devices for neonatal use have a diameter of the breathing gas through duct of 11 mm, whereas breathing tube connecting devices for respirators for adults may have a breathing gas through duct diameter of 15 mm or 22 mm.

Respirators for adults generally have a breathing mode for newborns. If a neonatal patient shall now be respirated with a respirator for adults, it is desirable that the breathing tube connecting device of the neonatal breathing tube, which is designed for a connection to a neonatal respirator, can be connected both to the neonatal respirator and to the respirator for adults. Moreover, it should be possible to produce the breathing tube connecting device in a simple and cost-effective manner.

SUMMARY OF THE INVENTION

Accordingly, the object of the present invention is to provide a breathing tube connecting device that is simple to produce, which eliminates the problem described above.

According to the present invention, this object is accomplished by a breathing tube connecting device for connecting a breathing tube to at least two respirators consisting of a base body with a breathing gas through duct embodied in the base body, a jacket body, which can be meshed with the base body in a positive-locking manner and thereby encloses at least a part of the base body in a coaxial manner, and a transponder, which is provided between the base body and the jacket body. The breathing gas through duct and jacket body are designed at least partly as a coupling section for a selective connection of the breathing tube to one of the at least two respirators. In this context, the transponder is defined as an element for wireless sending and for receipt of data.

The idea of the present invention is to provide a base body with a breathing gas through duct corresponding to the diameter of the neonatal breathing tube and a jacket body designed in terms of dimensions corresponding to the connection to the respective respirator for adults, whereby the base body can be combined with the jacket body provided for the corresponding respirator for adults and in the combination the base body and the jacket body are meshed in a positive-locking manner, such that a neonatal breathing tube can be connected by means of the breathing tube connecting device according to the present invention both to a neonatal respirator and to a respirator for adults.

The advantages gained with the present invention are especially that the breathing tube connecting device according to the present invention can be produced in a very cost-effective manner. In this case, a base body can be produced, which can be combined and can be meshed (engaged) in a positive-locking manner with a corresponding jacket body according to the respective respirator for adults in such a way that the breathing tube connecting device can be connected both to the neonatal respirator and to the respirator for adults. A respectively identical base body may thus be combined with a jacket body, which has a diameter required for connection to the corresponding respirator for adults. The breathing tube connecting device according to the present invention thus makes possible a connection of a breathing tube both to a first and a second respirator, whereby the first and second respirators have a different connecting structure. The first respirator is a neonatal respirator and the second respirator a respirator for adults. In addition, the respirator for adults has a breathing mode for the respiration of neonates.

The structure of the breathing tube connecting device according to the present invention is designed in such a way that both the outer surface of the base body and the inner wall of the jacket body have a preferably cylindrical design. This design makes possible a stable connection of the base body and jacket body. The base body and jacket body are connected in a positive-locking manner preferably by means of a meshing of a circumferential beading provided on the outer surface of the base body with a complementary circumferential groove provided on the inner wall of the jacket body. To prevent a rotation of the jacket body in relation to the base body after the meshing of the base body and jacket body in a positive-locking manner, particularly when connecting or disconnecting the breathing tube connecting device to or from the respirator, means that prevent rotation are provided in another embodiment of the device according to the present invention. For this, preferably the base body has a lug directed at right angles to the outer surface of the base body and the jacket body has a complementary cutout directed at right angles to its inner wall. The lug of the outer surface of the base body meshes with the cutout of the inner wall of the jacket body when they are connected in a positive-locking manner. A material of the base body and the jacket body preferably consists of polypropylene. As is well known, polypropylene is an elastic material that promotes the positive-locking connection of the base body and jacket body. In addition, the part of the breathing gas through duct of the base body directed toward a respirator and the outer surface of the jacket body run in a cone-shaped manner for an optimal connection of the breathing tube connecting device to a respirator.

The transponder is advantageously provided between the base body and jacket body. Transponders have a high heat sensitivity. Insertion into the base body or jacket body during a production of the base body or jacket body in the injection molding process is almost impossible without destroying its functions. A positioning of the transponder on the outer surface of the breathing tube connecting device, for example, by bonding, may, on the one hand, cause damage to the transponder during the connection of the breathing tube connecting device to the respirator, and, on the other hand, lead to an untightness of the respirator/patient connection.

The structure of the breathing tube connecting device according to the present invention does make it possible to position the transponder between the outer surface of the base body and the inner wall of the jacket body, such that the transponder is protected against damage by the jacket body of the breathing tube connecting device surrounding it.

Auxiliary means for positioning the transponder on the base body are preferably provided on the outer surface of the base body. For example, the circumferential beading provided on the outer surface of the base body can be provided as a positioning aid when mounting the transponder on the base body. The transponder is preferably mounted on a side of the base body pointing toward the respirator. Thus, passive transponders with a highly limited range may also be used. This may be, for example, an RFID transponder that has a range of ca. 18 mm.

The transponder is preferably mounted on the outer surface of the base body by means of a suitable bonding process. Bonding processes for mounting transponders on the surface of a certain part are known from the state of the art; hence, this will not be discussed in detail at this point. However, in a preferred process step shortly before completion or after the production of the base body by means of an injection molding process, provisions may also be made for mounting the transponder on the base body, while the base body preferably initially remains in an injection molding die after its production and the transponder is mounted onto the outer surface of the base body by means of a suitable injection molding technique, without the transponder being entirely surrounded by injection molding material.

In an especially preferred embodiment of the breathing tube connecting device, the transponder is equipped with a function for storing data. By means of the storage function of data, the transponder advantageously makes possible a filing of breathing parameters. For example, a respiration rate, a breath, a breathing pressure and/or an identification of the breathing tube can be filed as breathing parameters. When the respirator is changed, e.g., because of a change within the clinical area of the patient, the breathing tube remains at the patient. The data filed in the transponder are thus available with the breathing tube and make possible an automatic or semi-automatic setting of the breathing parameters required at this respirator when the breathing tube is connected to a different respirator. Thus, the setting parameters of a first respirator can be transmitted in a simple manner to a second respirator. Furthermore, data about forbidden parameters of other apparatuses can be filed in the transponder of the breathing tube connecting device. For example, a breathing mode for adults can be blocked when the neonatal breathing tube is connected to a respirator for adults after recognition of the neonatal breathing tube.

Furthermore, the transponder of the device according to the present invention makes it possible to detect and file such personal data as, for example, a identification number. By means of a patient identification number, a respirator connected to a clinical network can be set to the breathing parameters required for the corresponding patient.

In another embodiment of the breathing tube connecting device according to the present invention, parameters are transmitted for a guarantee of a perfect function of the breathing tube. For example, a shelf life of the breathing tube can be stored on the transponder and corresponding information can be sent to the user after the end of a time, e.g., a time determined and fixed for a guarantee of a perfect function of the breathing tube.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
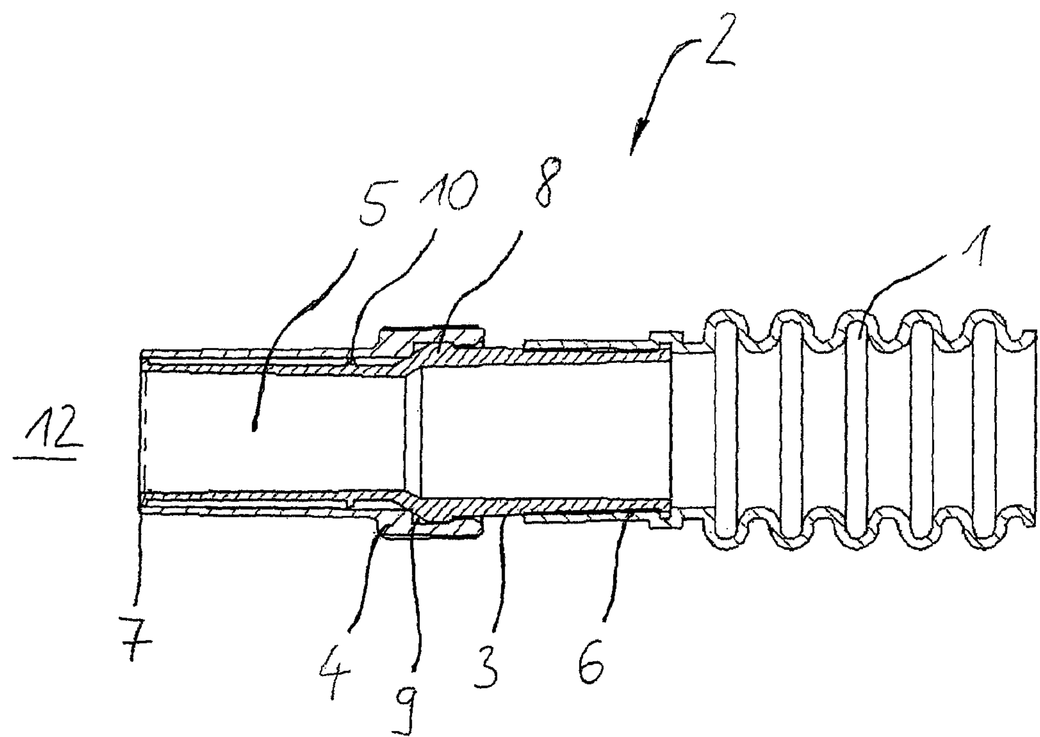
FIG. 1 is a simplified sectional view of the breathing tube connecting device according to the present invention in a first embodiment.

Referring to the drawings in particular, the breathing tube 1 shown in FIG. 1 is provided in its end area with a breathing tube connecting device 2, which has a base body 3 and a jacket body 4 enclosing a part of the base body 3 directed toward a respirator 12. A breathing tube fastening section 6, in which the breathing tube 1 is fixed, is formed in the area of the base body 3 on the breathing tube side. The base body 3 has a breathing gas through duct 5, whose through cross section essentially corresponds to the through cross section of the breathing tube 1 connected to the breathing tube fastening section 6. Both the outer surface of the base body 3 and the inner wall of the jacket body 4 of the breathing tube connecting device 2 shown in FIG. 1 have a cylindrical design.

In a middle area of the base body 3, a circumferential beading 8 is provided on the outside thereof, via which a positive-locking connection with a complementary circumferential groove 9 located on the inner wall of the jacket body 4, which is favorable from mechanical points of view, is achieved. To prevent a rotation of the jacket body 4 against the base body 3 when connecting or disconnecting the breathing tube connecting device 2 to or from a respirator 12, a lug 10 directed at right angles to an outer surface of the base body 3 is provided, which meshes with a complementary cutout directed at right angles to the outside of the jacket body 4. A snapping of the lug 10 of the base body 3 into the cutout of the jacket body 4 signals an accurate connection of the base body 3 and jacket body 4. The base body 3 and jacket body 4 are preferably made of polypropylene (PP) because of good elastic properties. However, it is also possible to make the base body 3 and the jacket body 4 out of other suitable materials.

Figure 2:
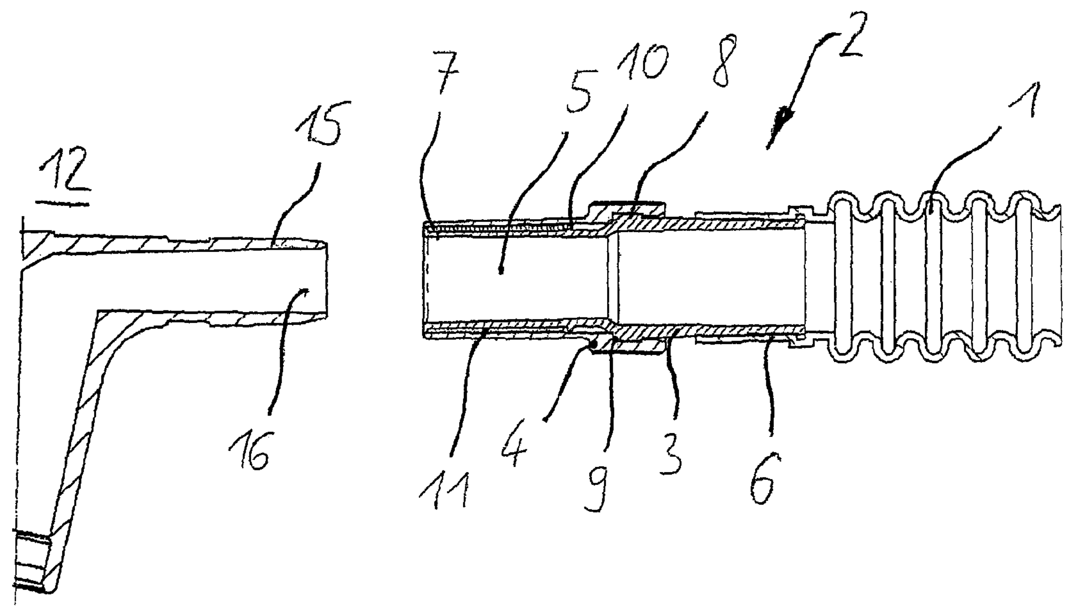
FIG. 2 is a simplified sectional view of the breathing tube connecting device according to the present invention for explaining a connection of a neonatal breathing tube to a neonatal respirator.
Figure 3:
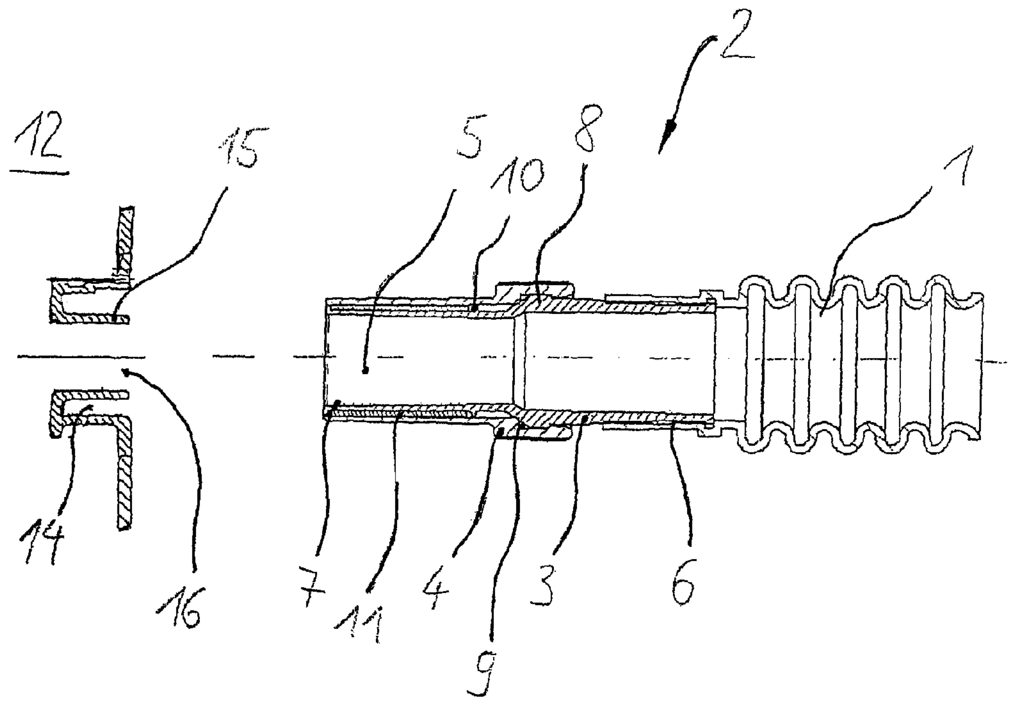
FIG. 3 is a simplified sectional view of the breathing tube connecting device according to the present invention for explaining a connection of a neonatal breathing tube to a respirator for adults.

For the purpose of explaining the connection of the breathing tube connecting device according to the present invention to a respirator 12, FIGS. 2 and 3 show a respirator-side connecting structure 16, which has a design essentially complementary to the coupling section 7 embodied by the base body 3 and jacket body 4. FIG. 2 shows a breathing tube connecting device 2 for connecting to a neonatal respirator 12. A neonatal respirator 12 is generally designed with a male connecting structure 16, which has a diameter of 11 mm. A respirator 12 for adults, as it is shown in FIG. 3, usually has, by contrast, a male and a female connecting structure 16, whereby the male connecting structure 16 has a diameter of 15 mm and the female connecting structure 16 has a diameter of 11 mm. The breathing tube connecting device 2 according to the present invention may advantageously connect a neonatal breathing tube 1 to a neonatal respirator 12 and to a respirator 12 for adults. In the connection of a breathing tube connecting device 2 of a neonatal breathing tube 1 to a connecting structure 16 of a neonatal respirator 12 schematically shown in FIG. 2, the coupling section of the breathing tube connecting device 2 identified by reference number 7 meshes with a pin section 15 of the connecting structure of the neonatal respirator 12. The coupling section 7 is formed by the inner wall of the base body 3, [i.e.] the breathing gas through duct 5. A part of the breathing gas through duct 5 of the base body 3 directed toward the respirator 12 advantageously has a cone-shaped design. The pin section 15 of the connecting structure 16 of the neonatal respirator 12 shown in FIG. 2 has a shape complementary to the coupling section 7.

During the connection of the breathing tube connecting device 2 of a neonatal breathing tube 1 to a connecting structure 16, as is schematically shown in FIG. 3, of the respirator 12 for adults, the coupling section 7 of the breathing tube connection device 2 meshes with a recess 14 and with the pin section 15 of the connecting structure 16 of the respirator 12 for adults. The coupling section 7 is formed by the inner wall of the base body 3 and the outer surface of the jacket body 4. With the breathing tube connecting device 2 according to the present invention, a neonatal breathing tube 1 can thus be connected both to the connecting structure 16 of the neonatal respirator 12 (shown in FIG. 2) and to the connecting structure 16 of a respirator 12 for adults (shown in FIG. 3). The outer surface of the jacket body 4 advantageously has, as shown in FIG. 3, a cone-shaped design and cooperates with the cone-shaped recess 14 of the connecting structure 16 of the respirator 12 for adults.

Figure 4:
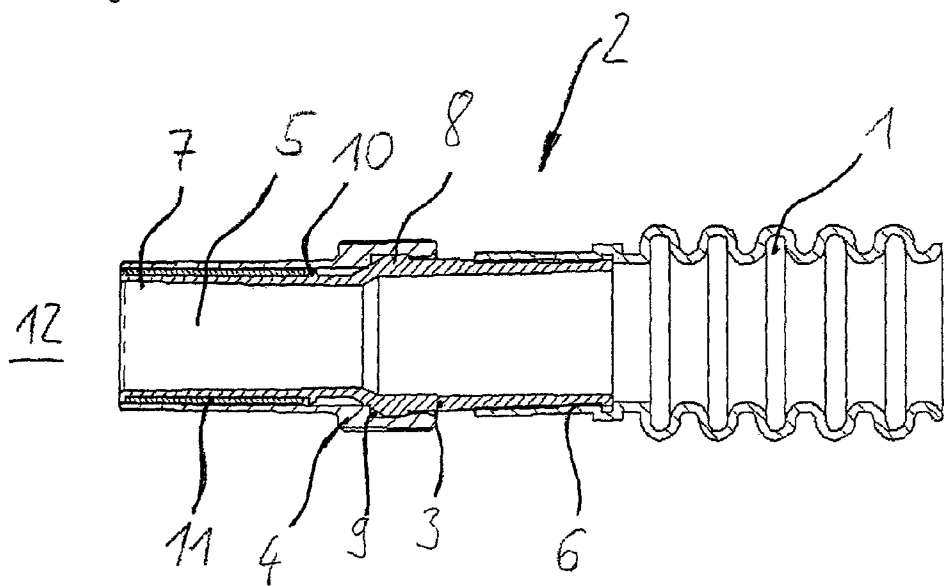
FIG. 4 is a simplified sectional view of the breathing tube connecting device according to the present invention in a second embodiment with a transponder.

FIG. 4 shows a very particularly preferred embodiment of the breathing tube connecting device 2. A transponder is provided between the outer surface of the base body 3 and the inner wall of the jacket body 4. The transponder 11 is used for the wireless sending and the wireless receipt of data and is additionally equipped with a function for storing data. The circumferential beading 8 provided on the outer surface of the base body 3 is used as a positioning aid during the mounting of the transponder 11 on the base body 3. It is thereby guaranteed that the transponder 11 has a reproducible position and is provided very close at one end of a side of the base body 3 pointing toward the respirator 12. This makes it possible to use passive transponders 11, for example, an RFID transponder 11 with a range of ca. 18 mm. The receipt and sending of data are thus optimally guaranteed. The transponder 11 of the breathing tube connecting device 2 according to the present invention of FIG. 4 makes it possible, by means of a data storage function, to advantageously file such breathing parameters as, for example, a respiration rate, a breath, a breathing pressure and/or a form of respiration. If only the breathing tube 1 is uncoupled from the neonatal respirator 12 and is coupled to a respirator 12 for adults, the breathing parameters of the neonatal respirator 12 stored on the transponder 11 can be transmitted to the respirator 12 for adults, or these breathing parameters are released to the respirator 12 for adults. A setting of too-high breathing pressures for newborns, as they are necessary for a respiration of adults, is thus ruled out. Furthermore, personal data, for example, a patient identification number can be stored with the transponder 11 of the breathing tube connecting device 2 according to the present invention. In case of a change of the clinical area and thus of the respirator, the breathing tube 1 remains at the patient. The data stored in the transponder 11 are thus available with the breathing tube 1 and make possible a transmission of the data to the respirator 12 when the breathing tube 1 is connected to the respirator 12 for adults. By means of a patient identification number, for example, a respirator 12 connected to a clinical network can be set to the breathing parameters required for the corresponding patient.

In another embodiment of the breathing tube connecting device 2 shown in FIG. 4, parameters for a guarantee of a perfect function of the breathing tube 1 are transmitted to the transponder 11. For example, the time of using the breathing tube 1 at the respective respirator 12 is measured and then sent to the transponder 11. Thus, the overall shelf life of the breathing tube 1 can be stored on the transponder 11 and after reaching a time duration that defines an end for the guarantee of the perfect function of the breathing tube 1, corresponding information can be sent to the user.

A preferred process for the manufacture of the breathing tube connecting device 2 according to the present invention is explained below based on the exemplary embodiment shown in FIG. 4. In a first process step, the base body 3 is produced by means of an injection molding process. The base body 3 has thereby a circumferential beading 8 protruding from the outer surface, which is used for the positioning of a transponder 11 to be mounted on the outer surface of the base body 3 in another process step. The transponder 11 is thereby mounted on a part of the outer surface of the base body 3 pointing toward the respirator 12. After that or in parallel thereto, the jacket body 4 is produced by means of an injection molding process. In another process step, the base body 3 is connected to the jacket body 4 in a positive-locking manner.

While specific embodiments of the invention have been described in detail to illustrate the application of the principles of the invention, it will be understood that the invention may be embodied otherwise without departing from such principles.

The invention claimed is:

1. A breathing tube connecting device for connecting a breathing tube to at least two respirators, the breathing tube connecting device comprising:

a base body with a breathing gas through duct embodied in the base body, said base body comprising a breathing tube fastening section connected to the breathing tube, said breathing tube fastening section being located at one end portion of said base body;

a jacket body, which is meshed with the base body in a positive-locking manner and thus encloses at least a part of the base body in a coaxial manner, said jacket body and said base body comprising a coupling section defining a selective respirator connection for connecting the breathing tube to one of the at least two respirators, said coupling section comprising a base body portion located at another end portion of said base body and a jacket body portion located at an end portion of said jacket body being adjacent to said base body portion.

2. A breathing tube connecting device in accordance with claim 1, further comprising:

a transponder provided between the base body and the jacket body; and the breathing tube connected to said base body wherein a through cross section of the breathing gas through duct substantially corresponds to a through cross section of the breathing tube, said breathing tube having a breathing tube end portion, said breathing tube end portion having an inner breathing tube surface, wherein an outer surface of the base body engages said inner breathing tube surface, said coupling section of said base body and said jacket body comprising an inner base body surface of said base body and a jacket body outer surface of said jacket body, said inner base body surface defining an inner connection and said jacket body outer surface defining an outer connection, said breathing tube connecting device being connected to one of the at least two respirators via said inner connection, said breathing tube connecting device being connected to another one of the at least two respirators via said inner connection and said outer connection.

3. A breathing tube connecting device in accordance with claim 1, wherein a part of the breathing gas through duct directed toward the at least two respirators runs in a cone-shaped manner and an outer surface of the base body has a cylindrical design.

4. A breathing tube connecting device in accordance with claim 1, wherein an inner wall of the jacket body has a cylindrical design and an outer surface runs in a cone-like manner.

5. A breathing tube connecting device in accordance with claim 1, wherein the base body and jacket body are connected in the positive-locking manner by means of a meshing of a circumferential bearing provided on an outer surface of the base body with a complementary circumferential groove provided on an inner wall of the jacket body, wherein said inner wall of said jacket body extends from said another end portion of said base body to a position adjacent said circumferential bearing, said inner wall having a first inner wall end portion and a second inner wall end portion, said first inner wall end portion being opposite said another end portion of said base body, said second inner wall end portion being adjacent to said circumferential bearing.

6. A breathing tube connecting device in accordance with claim 1, further comprising rotation preventing means for preventing a rotation of the jacket body in relation to the base body, wherein said coupling section of said base body comprises an inner surface of said base body and said coupling section of said jacket body comprises an outer surface of said jacket body, said inner surface being in contact with an outer surface of a connecting structure of said one of the at least two respirators in a first respirator connected state, said inner surface being in contact with another outer surface of another connecting structure of another one of the at least two respirators in a second respirator connected state, said outer surface of said jacket body engaging a portion of said another connecting structure in said second respirator connected state, said breathing tube being located at a spaced location from said jacket body.

7. A breathing tube connecting device in accordance with claim 6, wherein the base body has a lug directed at right angles to the outer surface and the jacket body has a complementary cutout directed at right angles to the inner surface forming said rotation preventing means.

8. A breathing tube connecting device in accordance with claim 1, wherein the base body and the jacket body consist of polypropylene.

9. A breathing tube connecting device in accordance with claim 2, wherein the transponder encloses the base body in a coaxial manner.

10. A breathing tube connecting device in accordance with claim 2, wherein the outer surface of the base body has auxiliary means for the positioning of the transponder on the base body.

11. A breathing tube connecting device in accordance with claim 2, wherein the transponder is provided on a side of the base body pointing toward the at least two respirators.

12. A breathing tube connecting device in accordance with claim 2, wherein the transponder contains a storage element.

13. A breathing tube connecting device in accordance with claim 12, wherein parameters of a first respirator are transmitted to a second respirator.

14. A process for connecting a breathing tube connecting device, the process comprising:

providing respirators including a first respirator having a first connecting structure and a second respirator having a second connecting structure with the first connecting structure being a different connecting structure from the second connecting structure;

providing a breathing tube connecting device for connecting a breathing tube to at least two respirators, the breathing tube connecting device comprising a base body having an inner base body surface defining a breathing gas through duct and a jacket body, said jacket body engaging the base body in a positive-locking manner and said jacket body enclosing at least a part of the base body in a coaxial manner, whereby an end portion of said base body and an end portion of said jacket body define at least a portion of a coupling section of said breathing tube connecting device for a connection of the breathing tube to one of the at least two respirators, said base body having a breathing tube connecting end portion, said breathing tube connecting end portion being located opposite said end portion of said base body; and connecting the breathing tube connecting device to one of the first connecting structure and the second connecting structure, wherein said breathing tube is connected to said one of the at least two respirators via said breathing tube connecting device, at least a portion of said inner base body surface engaging at least a portion of said one of the first connecting structure and the second connecting structure.

15. A process in accordance with claim 14, wherein providing the breathing tube connecting device includes:

engaging the jacket body with the base body in the positive-locking manner by means of a meshing of a circumferential bearing provided on an outer surface of an base body with a complementary circumferential groove provided on an inner wall of the jacket body; and connecting the breathing tube to said breathing tube connecting end portion of said base body wherein a through cross section of the breathing gas through duct substantially corresponds to a through cross section of the breathing tube.

16. A process in accordance with claim 14, wherein a part of the breathing gas through duct directed toward the respirators is cone-shaped with an outer surface of the base body that is cylindrical; and an inner wall of the jacket body is cylindrical design and an outer surface of the jacket body has a cone-shape, said breathing tube having a breathing tube end portion, said breathing tube end portion having an inner breathing tube surface, wherein the outer surface of said base body engages said inner breathing tube surface, said coupling section of said base body and said jacket body comprising the inner base body surface of said base body and the outer surface of said jacket body, said inner base body surface defining an inner connection and said jacket body outer surface defining an outer connection, said breathing tube connecting device being connected to the first connecting structure and the second connecting structure via said inner connection in a first respirator connected state, said breathing tube connecting device being connected to the another of the first connecting structure and the second connecting structure via said inner connection and said outer connection in a second respirator connected state.

17. A process in accordance with claim 14, wherein engaging the jacket body with the base body includes providing a rotation preventing means for preventing a rotation of the jacket body in relation to the base body, said coupling section comprising an inner surface of said base body and an outer surface of said jacket body, said inner surface being in contact with an outer surface of said one of said first connecting structure and said second connecting structure in a first respirator connected state; and further comprising:

connecting said breathing tube connecting device to another one of said first connecting structure and said second connecting structure in a second respirator connected state, said inner surface being in contact with another outer surface of another one of said first connecting structure and said second connecting structure in said second respirator connected state, said outer surface of said jacket body engaging a portion of another one of said first connecting structure and said second connecting structure in said second respirator connected state, said coupling section being located at said end portion of said base body, said jacket body being located at a spaced location from said breathing tube with respect to a longitudinal axis of said base body.

18. A process in accordance with claim 14, further comprising:

a transponder provided between the base body and the jacket body, wherein the transponder encloses the base body in a coaxial manner and an outer surface of the base body has auxiliary means for the positioning of the transponder on the base body.

19. A process in accordance with claim 14, further comprising:

a transponder provided between the base body and the jacket body, wherein the transponder is provided on a side of the base body pointing toward the respirators.

20. A process in accordance with claim 14, further comprising:

a transponder provided between the base body and the jacket body, wherein the transponder contains a data storage element and wherein parameters of the first respirator are transmitted to the second respirator with transmission including a wireless sending and or receipt of data.

* * * * *